United States Patent [19]

Pinto

[11] Patent Number: 4,664,125
[45] Date of Patent: * May 12, 1987

[54] FLOW-OCCLUDING METHOD FOR THE DIAGNOSIS OF HEART CONDITIONS

[76] Inventor: John G. Pinto, 17812 Creicente Way, San Diego, Calif. 92127

[*] Notice: The portion of the term of this patent subsequent to Jun. 3, 2003 has been disclaimed.

[21] Appl. No.: 868,507

[22] Filed: May 30, 1986

Related U.S. Application Data

[63] Continuation-in-part of Ser. No. 608,798, May 10, 1984, Pat. No. 4,592,364.

[51] Int. Cl.$^4$ .............................................. C61B 5/02
[52] U.S. Cl. .................................. 128/672; 128/668; 128/695; 128/710
[58] Field of Search ................ 128/668, 672, 695, 710

[56] References Cited

U.S. PATENT DOCUMENTS 4,223,682  9/1980  Sherman ............................ 128/672
4,592,364  6/1986  Pinto .................................. 128/672

OTHER PUBLICATIONS

Randall et al., "Proceedings of the IEEE," vol. 63, No. 10, pp. 1399-1403 (Oct. 1975).

Primary Examiner—Andrew H. Metz
Assistant Examiner—A. Pal
Attorney, Agent, or Firm—Charmasson & Holz

[57] ABSTRACT

A method for analyzing the biomechanical behavior of the cardiac muscle and for diagnosing pathological conditions of the heart. The apparatus measures and records the rise and fall of intra-ventricular isovolumetric pressure monitored by a transducer installed at the tip of a cardiac catheter. The pressure versus time recordings during both the systolic and diastolic phases are mathematically analyzed, and two parameters indicative of the biomechanical conditions of the muscle are derived. The parameters are then plotted against each other on a map in which diagnostic zones of various normal and pathological heart conditions are delineated. The cardiac catheter is fitted with a balloon inflation valve used to close the aortic port during a single heartbeat in order to override the aortic valve and maintain the isovolumetric condition during contraction and relaxation of the cardiac muscle organ.

9 Claims, 6 Drawing Figures ns
FLOW-OCCLUDING METHOD FOR THE DIAGNOSIS OF HEART CONDITIONS

PRIOR APPLICATION

This application is a continuation-in-part of application Ser. No. 608,798, filed May 10, 1984, to be issued as U.S. Pat. No. 4,592,364.

FIELD OF THE INVENTION

This invention relates to medical apparatuses such as instruments used in the diagnosis of pathological disorders through recording and analysis of signals representing physiological activities. More specifically, the invention relates to instruments designed to analyze the behaviour of the cardiac muscle.

BACKGROUND OF THE INVENTION

In-vitro studies of muscular tissue and, in particular cardiac muscle bundles have been directed toward the understanding of the mechanical characteristics of the contracting phenomenon.

It was thought that once these characteristics had been defined, the mechanical behaviour of a healthy organ could be represented in mathematical terms. Some of these terms could then be used as criteria in the diagnostic of pathological conditions.

The inventor focused his study on the analysis of the inotropy (from the Greek is, inos fiber; and tropos, behaviour) of the cardiac muscle, i.e. its contractility.

Traditionally, the behaviour of the cardiac muscle has been analyzed by measuring the absolute values of the systolic and diastolic blood pressures and of the pulse rate; and by listening to auditory manifestations of the muscle valve activity. Electrocardiography provides only a gross inferential tool for the diagnosis of pathological heart conditions. Studies of time and displacement dependency in the behaviour of the cardiac organ have mainly been directed to the interpretation of force-versus-velocity curves, and the potential use of a theoretical maximum velocity parameter (obtained by converging extrapolations of a family of force-velocity curves) as an indicator of organ health. None of the previous time-dependence studies have suggested a practical interpretation of the consistent parameters around which this invention is implemented.

SUMMARY OF THE INVENTION

A simple phenomenological model of the contracting cardiac muscle has been developed which is capable of simulating most major mechanical attributes of the contraction phenomenon. From this model two critical parameters have been isolated. The first, y is indicative of the delayed time response of the cardiac muscle to the signal initializing contraction or relaxation. The second, x represents the inotropic state of the muscle, i.e. its ability to response to the and the excitation and the particular mechano-chemical characteristic of that response.

These parameters can be derived from the continuous measurement of the intra-ventricular pressure during both the systolic and diastolic phases of the heart movement, according to the formula:

$$P(V,t) = B(V)t^y e^{-xt}$$

wherein P, is the intra-ventricular pressure as a function of the volume (V) and time (t); B represents the influence of the muscle length as a function of the volume (V) on the force of contraction; y is the excitation-contraction coupling parameter; and x is the inotropic coefficient.

It can be shown that the time Tmax necessary to reach peak pressure is equal to the ratio of y over x.

It is the principal object of the invention to provide an apparatus for analyzing the biomechanical behaviour of the cardiac muscle and for diagnosing its pathological conditions.

It is also an object of the invention to provide an apparatus for conducting clinical studies of the heart organ on live subjects, and in-vitro studies of muscular tissue samples.

A further object of the invention is to provide such an apparatus which calculates the y and x parameters for a particular muscle contracting phenomenon, and which uses them as criteria for the diagnosis of pathological conditions.

Another object of this invention is to provide a cardiac muscle analyzing apparatus which relies strictly on pressure-time dependency observations and uses only simple and reliable measurement of time and relative pressure variation.

These and other valuable objects are achieved by means of a simple monitoring device which records samples of intraventricular or arterial pressures during the systolic and diastolic phases of the heart movement; then, conducts a analytical study of the pressure-versus-time variations in order to extract the parameters characteristic of the muscle inotropy.

On occasion, it may be necessary to gage the muscle function from records of pressure obtained during true isovolumetric contraction of the heart. In order to obtain a true isovolumetric measurement of the hemodynamic pressure the invention uses a balloon inflated valve arrangement mounted on a aortic catheter distally form the pressure sensor which is introduced into the left ventricle. The balloon is inflated in a timely fashion to completely block the flow of blood during one heart beat thus producing a true isovolumetric heart beat.

DESCRIPTION OF THE PREFERRED EMBODIMENT OF THE INVENTION

Figure 1:
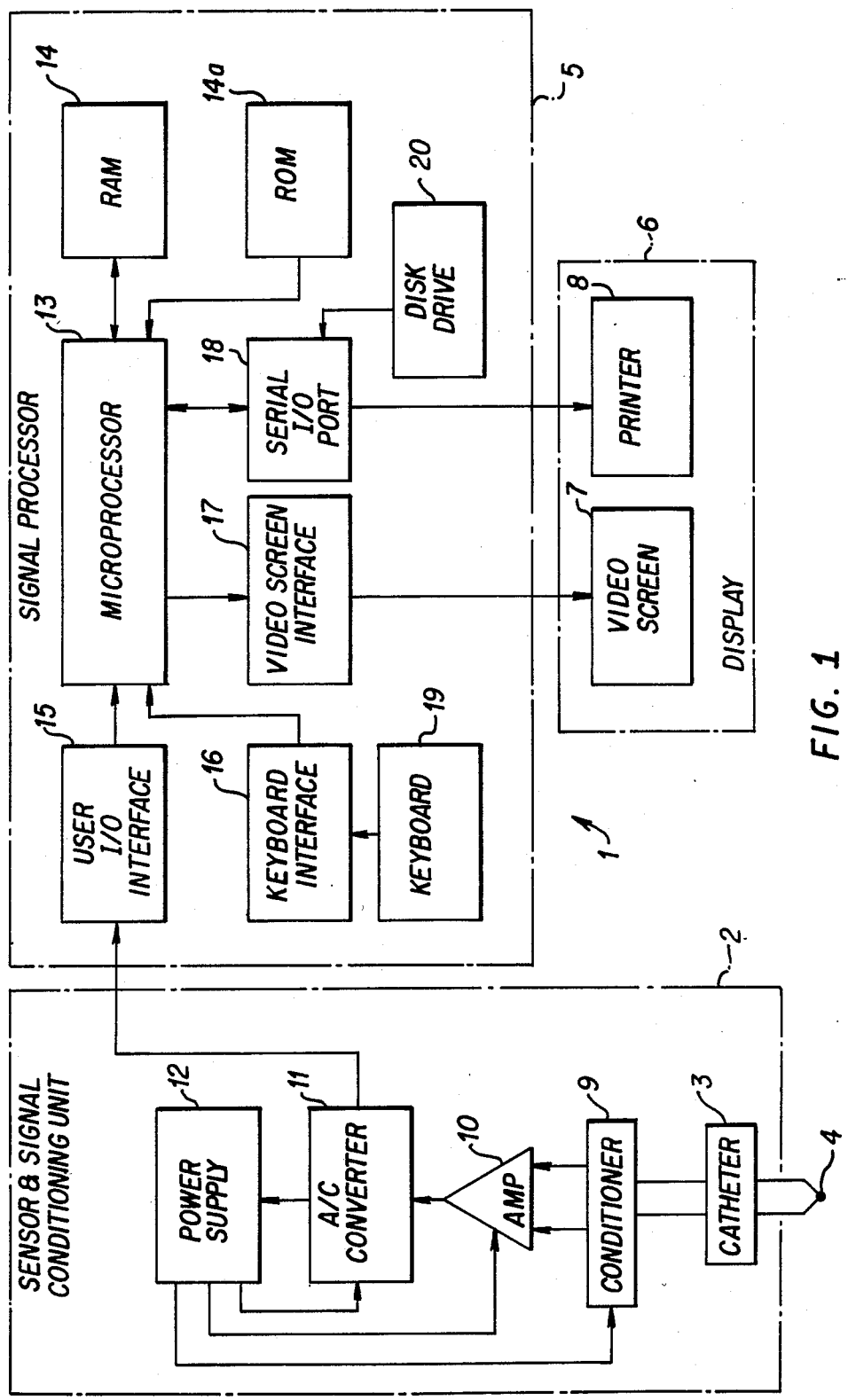
FIG. 1 is a general block diagram of a cardiac inotropy analyzing apparatus which constitutes the preferred embodiment of the invention.

Referring now to the drawing, there is shown in FIG. 1 a general block diagram of the cardiac inotropy analyzing apparatus 1 which is divided into three major components. The sensor and signal-conditioning unit 2 comprises a pressure monitoring unit with a sensor 4 which is or inserted into the heart left ventricle by means of a catheter 3 as will be further explained below. The associated electronic circuit converts the monitored pressure into a digitally-coded signal which is fed to the second major component, the signal processor 5.

The signal processor analyzes the pressure signal and extracts the excitation-contraction coupling parameter y and the inotropic coefficient x from the time-response curve representing the pressure variation during both the systole and diastole. The signal processor 5 also creates a graphic interpretation of the pressure signal and parameters, then controls the last major component, the display 6.

The display includes a video screen 7 and a printer 8.

More specifically, the sensor 4 and signal conditioning unit 2 comprises, in connection with the sensor 4 a interface unit 9 such as a strain gage bridge, connected to the input of a differential signal amplifier 10. The output of the amplifier is fed to an analog-to-digital converter 11 which produces a corresponding binary-coded signal. These circuits are energized by a power supply 12.

Typically, a pressure transducer with a resolution of 2.5 millimeters of mercury and a linearity of one percent of full scale; a differential amplifier with corresponding resolution and linearity; and a eight-bit analog-to-digital converter with a twenty microsecond conversion time, are suggested.

The signal processor 5 comprises a general purpose programmable eight-bit microprocessor 13 equipped with sixty-four kilobytes of random-access memory (RAM) 14, and a read-only memory (ROM) 14a holding a standard operating software and common programming language interpreter or compiler.

The signal processor 5 also comprises a standard user input-output interface 15, a keyboard input interface 16, a video screen output interface 17 and a serial input-output port 18.

A keyboard 19 and disk-drive 20 complete the list of basic components of the system. The disk-drive 20 is used to read the application program recorded on diskettes, as well as some reference parameters. The disk-drive can also be used to record in digital form the information sent to the display unit 6. Alternately, the application program could be stored permanently in a section of the ROM 14a.

The operation of the signal processor 5 in the analysis of the digitized pressure measurement data supplied by the sensor and signal-conditioning unit will be described in detail with reference to FIGS. 2 and 3.

Figure 2:
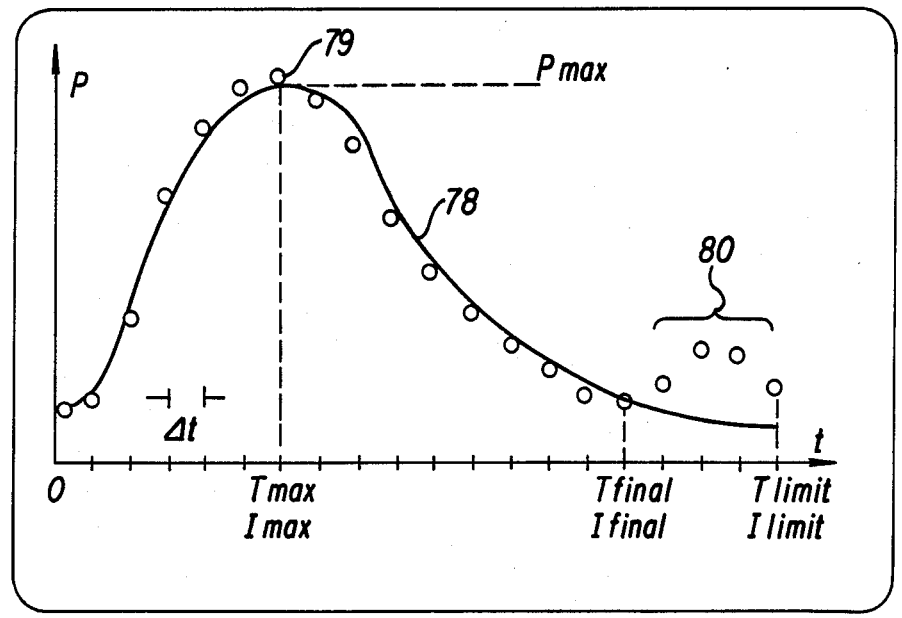
FIG. 2 is a graph of the intra-ventricular or arterial pressure measurements as a function of time.

The graph of FIG. 2 illustrates the blood pressure variation during the systolic and diastolic phases of the heart cycle. The full curve 78 represents the theorical function:

$$\text{Pressure} = (P) = Bt^y e^{-xt}$$

for a particular individual based on accepted norms for his age and sex group.

The dotted line 79 represents the actual measurement samples taken by the apparatus. The rising transient 80 at the bottom of the curve is due to the opening of the mitral valve and/or valvular interaction and aortic recoil.

B represents a factor characteristic of the size of the particular organ under observation and is proportional to the amplitude of the pressure. As previously explained, the two parameters y and x denote the particular characteristics of the contraction phenomenon.

Figure 3A:
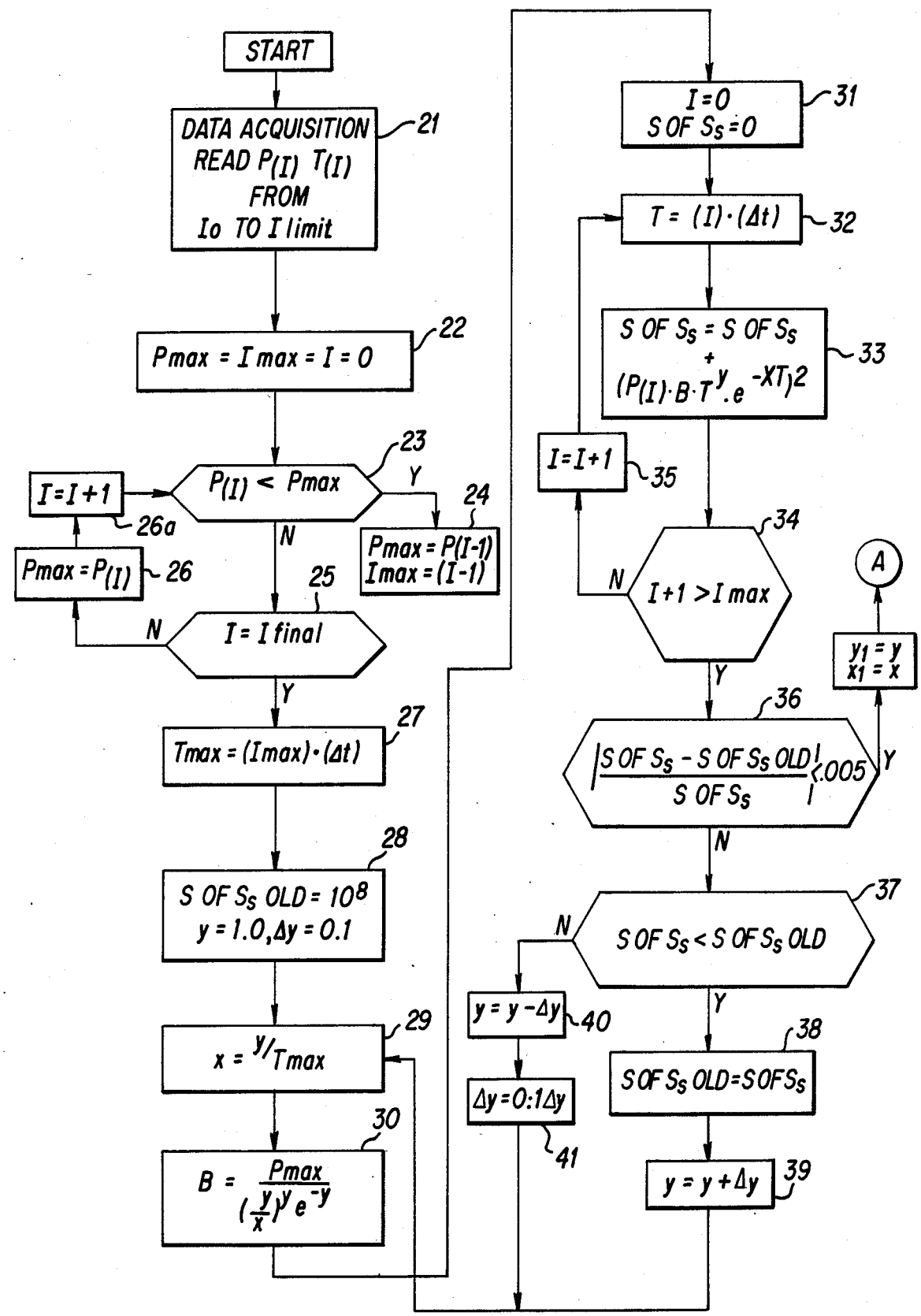
FIGS. 3a and 3b give the flow diagram of the application computer program controlling the operation of the apparatus.
Figure 3B:
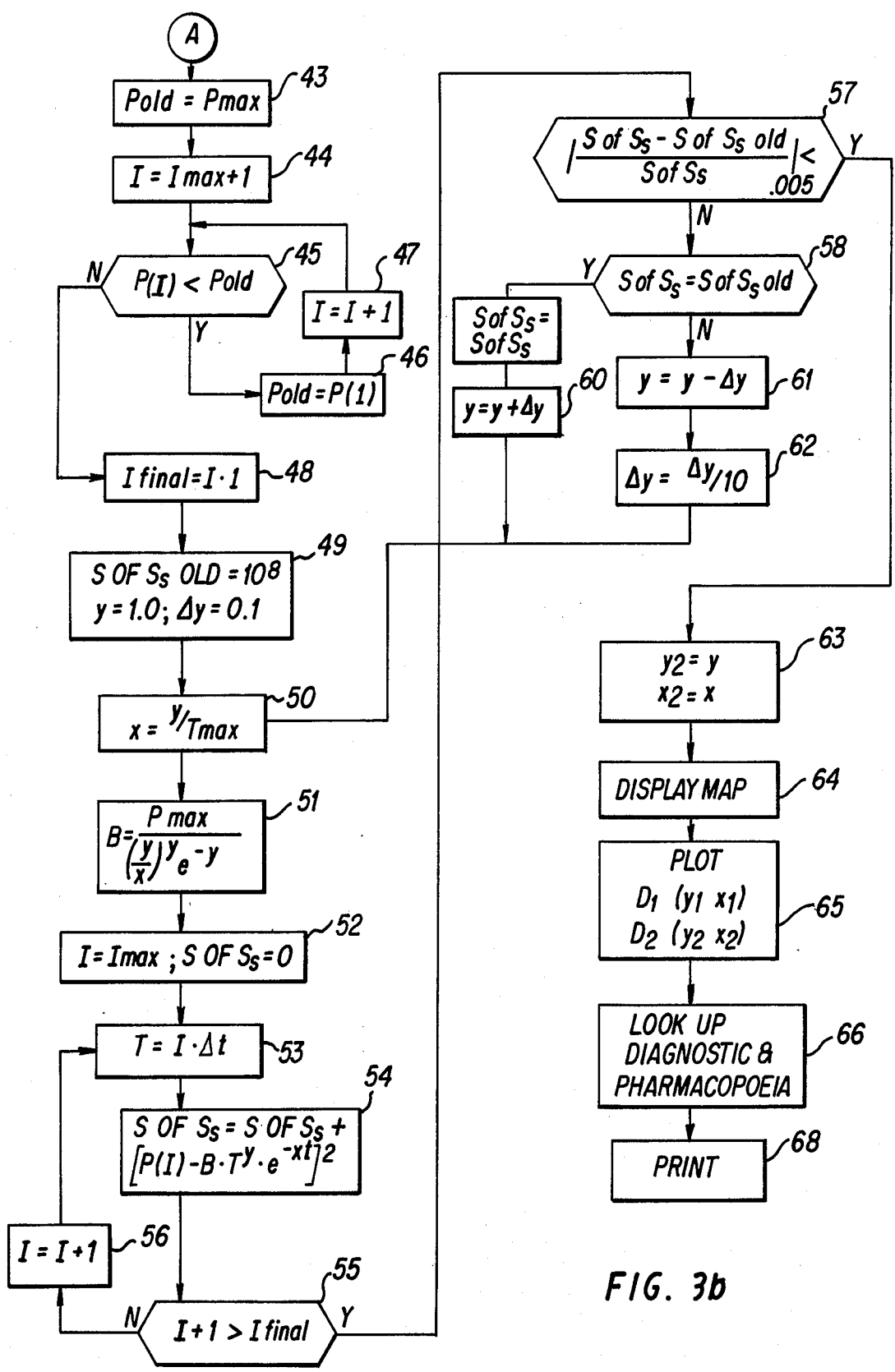

The data obtained by means of the sensor 4 and the sensor and signal conditioning unit 2 shown in FIG. 1 are acquired and analyzed by the signal processor 5 in accordance with the flow diagram of FIG. 3a and 3b.

The data acquisition phase 21-27 is done in a series of samplings whose sequence and number are determined by the index I.

As successive readings of the pressure P and time t are taken, the apparatus searches for a drop in the pressure 23, indicating that the maximum pressure Pmax has been reached. The peak pressure is noted 24, as well as the corresponding time Tmax 27, by multiplying the number of samplings taken Imax by the sample period.

The apparatus then seeks to determine the y and x parameters of the theoretical function curve which most closely fits the acquired data, using an iterative sum of squares approximation method.

The program sets an initial trial value 28 for old sum of squares ($10^8$) and parameter y (1.0) and $\Delta y$ (0.1). These values are then used for the computation 29, 30 of parameter x and factor B according to the equations:

$$x = y/T\text{max}; \quad B = \frac{P\text{max}}{e^{-y}} \cdot \left[\frac{x}{y}\right]^y$$

The data point index I is then initialized 31 for sum squares equal to zero. Then the sum squares of differences between the sampled and theoretical pressures are computed 32-41 in iterative form until the detection 36 of changes in value of less than 0.005 indicates a converged value of y. At that point, the systolic values y, and x, of the parameters are noted 42.

During this process the value of sum squares is tested 37 to assure that it continues to decrease as y is increased 39. If, instead, the sum square increases, they y is reduced 40,41; and a smaller y increment is used successively if necessary, until the converged value of y is achieved.

The analysis of the diastolic phase samplings now begins with the initialization 43-44 of the index.

The samples are taken until the detection of the valve transient 80 which appears near the bottom end of the diastolic drop. The iterative search 45-48 for the transient continues so long as the pressure drops 45.

The curve fitting steps 49-63 mirror those 28-42 used during the systolic phase, with the difference that the index I goes from Imax at peak pressure to Ifinal when the valve transient is detected; instead of from I0 to Imax as in the first phase.

A second set of parameters $y_2$, $x_2$ are then noted for the diastolic phase.

The theoretical pressure curve and the sample measurements shown in FIG. 1 may be displayed on the video screen 7 and/or the printer screen 8 as the data is being acquired.

A trained operator may, upon simple observation of these graphs, draw various conclusions as to the condition of the organ under observation.

The diagnosis phase of the program 64-68, however, provides a more powerful tool for the systematic interpretation of the parameters, leading to a direct formulation of diagnostic and therapeutic indications fetched from pre-recorded data based on accumulated experience.

Figure 4:
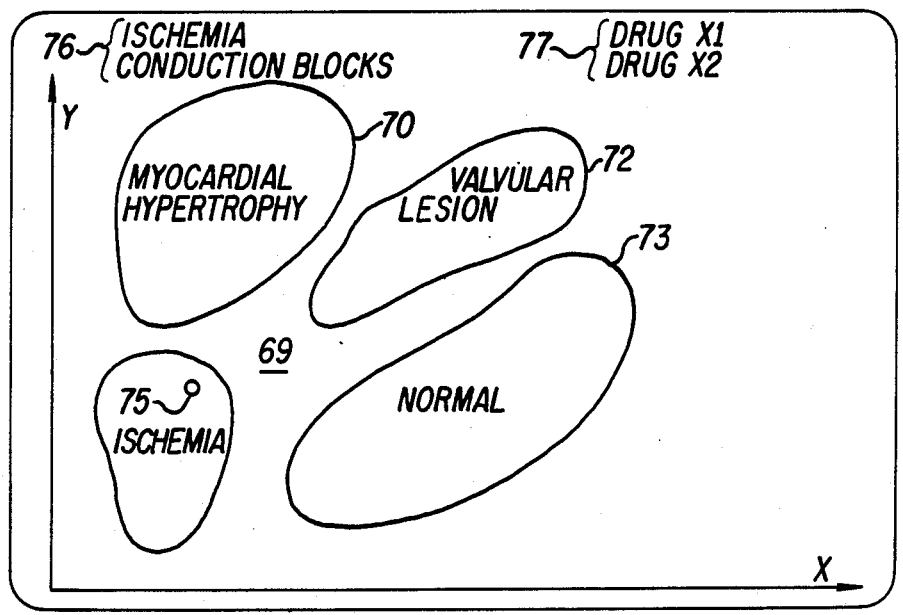
FIG. 4 is illustrating a diagnosing display of the contracting delay and inotropic parameters.

FIG. 4 illustrates the type of displayed or printed information which the apparatus can generate based upon the respective values of y and x.

The final diagnostic phase begins with the display of a map 69 generated from data pre-stored either in the ROM 14a or read by the disk-drive 20.

The map appears on the drawing as the background of FIG. 4. Various zones delineate the area indicative of various pathologies such as myocardial hypertrophy 70, ischemia 71, valvular lesion 72 etc. A normalized zone 73 corresponds to the parameter values of an healthy individual in the patient's age and sex group.

These various zones would be displayed as functions of the actual set of parameters being interpreted, the diagnosis goals as well as the patient's vital statistics. These various criteria can be entered according to well-known routines via the keyboard 19.

Next one or more indicators 74–75 are placed 65 on the map 67 by coupling any two parameters $y_1$, $x_1$, $y_2$, $x_2$ and ploting one against the other within each pair.

Pathological conditions are pointed out as the indicators 74–75 appears to fall within the respective zones. The location and size of each zone may change as clinical experience accumulates in the diagnosis of various heart conditions.

It should be understood that the territory of each zone 70–73 is predicated upon the predetermined interpretation of each pair of parameters. The location and size of each zone may change as various indicators are displayed.

The coordinates of each indicator are then used to direct the system 66–67 to a stored look-up table, from which printable diagnostic messages 76 or pharmacopoeia 77 may be extracted and printed 68.

Figure 5:
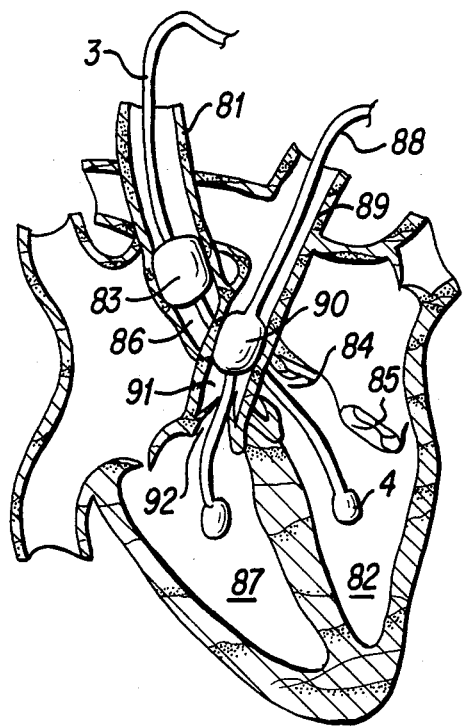
FIG. 5 is a diagrammatical illustration of the sensor and valve catheter positioning to obtain isovolumetric measurements.

Referring now to FIG. 5, the measurement of truly isovolumic hemodynamic pressure process will now be explained. The aortic catheter 3, having at its tip the pressure sensor 4, is inserted through the aorta 81 by way of the carotid or any other artery into the left ventricle 82. The catheter also carries a balloon inflation valve 83 at a short distance from the sensor 4, and positioned within discharge port 86 right behind the aortic valve 84. Catheters with a combination of pressure sensor and balloon inflation valve are currently indicated for assessment of hemodynamic conditions, such as the devices sold under the SWAN-GANZ trademark by American Edwards Laboratories, and could be easily modified and adapted for use according to the invention. The illustration of FIG. 5 shows the heart between the systolic and diastolic phases when the aortic valve 84 is about to close and the mitral valve 85 is closed. Actually the balloon inflation valve 83 is kept inflated for one full cardiac cycle. Given its position at the aortic port at a short distance from the aortic valve, it will override the latter and insure isovolumetric measurements. These measurements are not affected by the movement of the aortic valve or by the condition of the aortic network but reflect the true condition of the cardiac muscle organ itself.

It should be understood that the diagnostic process is not limited to the illustrative examples discussed above. Various other combinations and subcombinations of parameters and other factors particular to the patient may be used to address other types of prestored diagnostic and therapeutic indications for instance, true isovolumetric pressure of the right ventricle 87 could be obtained by inserting a catheter 88 through the pulmonary artery 89 with the valve 90 positioned in the discharge port 91 of the ventricle immediately behind the pulmonary valve 92. The apparatus, thus implemented constitutes a powerful tool in the hands of scientists for further exploration of the cardiac muscle behaviour and the refinement of the diagnostic interpretations of the suggested parameters. As more knowledge is acquired through clinical use of the apparatus on live individuals, as well as applications to in-vitro studies of the cardiac tissues, the practice of this invention may lead to simple and very reliable early diagnosis of pathologies which have been impossible to detect in their early manifestations.

The various hardware components of the apparatus may be selected from commercially available units. The system operating program, data input and output routine and user language assemblers do not differ from standard well-known processes. The implementation of the application programs in accordance with the instant disclosure is well within the ordinary skill of those knowledgeable in the arts of data processing.

The illustrative embodiment described above could be modified and improved, and other related apparatuses may be devised according to the invention and within the scope of the appended claims.

What is claimed is:

1. A method for analyzing the biomechanical behaviour of a subject's cardiac muscle and for diagnosing its pathological conditions which comprises:
   introducing a pressure sensor into one of the subject's ventricles;
   positioning a balloon inflation valve in the discharge port of said ventricle;
   closing said valve during at least one cycle of systolic or diastolic pressure;
   recording the pressure values derived from the sensor during said cycle;
   plotting said values in relation to time; and
   mathematically analysing said plotted values and deriving at least one parameter indicative of the condition of the cardiac muscle from the shape of the curve representing the variations of said values during said cycle by interpreting said curve as a theoretical pressure-function (P) varying in time (t) with changes of ventricular volume (V) according to a phenomenological model equation:

$$P(V,t) = B(V)t^y e^{-xt}$$

wherein B is a factor corresponding to the influence of the cardiac muscle size, y represents a first parameter indicative of the excitation-contraction delay, and x represents a second parameter indicative of the inotropic characteristic of the muscle; and computing the x and y parameters which most closely fit the curve.

2. The method claimed in claim 1, wherein the step of interpreting comprises:
   computing paired values of said parameters corresponding to a curve of the phenomenological model equation which most closely fits the variations of said signals.

3. The method claimed in claim 2, wherein said step of interpreting comprises computing a first set of values for said parameters corresponding to the signal recorded during the systolic phase, and a second set of values for said parameters corresponding to the signal recorded during the diastolic phase.

4. The method claimed in claim 3 which further comprises plotting one of said parameters against the other.

5. The method claimed in claim 4 wherein the step of plotting comprises forming a diagnostic map having the scaled value of each of said parameters as respective vertical and horizontal coordinates.

6. The method claimed in claim 5 which further comprises delineating in said map various zones corresponding to pathological muscle conditions; and placing on said map at least one mark having for coordinates the calculated values of said parameters.

7. The method claimed in claim 4 which further comprises:

storing a plurality of diagnosis messages;

addressing at least one of said stored messages in function of said first and second parameters; and displaying said message.

8. The method claimed in claim 2, wherein the step of introducing a pressure sensor comprises introducing a catheter equipped with a pressure sensor in the left ventricle through the aorta; and the step of positioning a balloon inflation valve comprises installing said valve along said catheter distally from said sensor behind the aortic valve.

9. The method claimed in claim 2, wherein the step of introducing a pressure sensor comprises introducing a catheter equipped with a pressure sensor through a pulmonary artery into the right ventricle; and the step of positioning a balloon inflation valve comprises installing said valve along said catheter distally from said sensor behind the pulmonary valve.

* * * * *